United States Patent
Levy

(10) Patent No.: US 8,632,582 B2
(45) Date of Patent: Jan. 21, 2014

(54) REMOVABLE AND/OR RETRIEVABLE STENTS AND KITS

(75) Inventor: Michael J. Levy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 181 days.

(21) Appl. No.: 13/070,680

(22) Filed: Mar. 24, 2011

(65) Prior Publication Data

US 2012/0071987 A1   Mar. 22, 2012

Related U.S. Application Data

(60) Provisional application No. 61/317,406, filed on Mar. 25, 2010.

(51) Int. Cl.
    *A61F 2/82* (2013.01)
    *A61F 2/84* (2006.01)

(52) U.S. Cl.
    USPC ........................................... 623/1.15

(58) Field of Classification Search
    USPC ............... 623/1.11, 1.12, 23.64, 23.7, 903; 606/108, 192, 194, 198
    See application file for complete search history.

(56) References Cited

U.S. PATENT DOCUMENTS

| 4,315,509 A * | 2/1982 | Smit ............................ 606/108 |
| 4,733,665 A | 3/1988 | Palmaz |
| 4,739,762 A | 4/1988 | Palmaz |
| 5,102,668 A * | 4/1992 | Eichel et al. ................. 424/490 |
| 5,195,984 A | 3/1993 | Schatz |
| 5,334,208 A | 8/1994 | Soehendra et al. |
| 5,725,572 A | 3/1998 | Lam et al. |
| 5,735,871 A | 4/1998 | Sgro |
| 5,755,781 A | 5/1998 | Jayaraman |
| 5,853,419 A | 12/1998 | Imran |
| 5,861,027 A | 1/1999 | Trapp |
| 6,007,573 A | 12/1999 | Wallace et al. |
| 6,059,810 A | 5/2000 | Brown et al. |
| 6,099,561 A | 8/2000 | Alt |
| 6,200,337 B1 | 3/2001 | Moriuchi et al. |
| 6,206,916 B1 | 3/2001 | Furst |
| 7,320,703 B2 * | 1/2008 | DiMatteo et al. ............ 623/1.12 |
| 8,066,715 B2 | 11/2011 | Ducharme |
| 2005/0131515 A1 | 6/2005 | Cully et al. |
| 2006/0190075 A1 | 8/2006 | Jordan et al. |
| 2006/0276887 A1 | 12/2006 | Brady et al. |
| 2007/0129719 A1 | 6/2007 | Kendale et al. |
| 2009/0093822 A1 | 4/2009 | Ducharme |
| 2011/0093002 A1 * | 4/2011 | Rucker et al. ................. 606/198 |

OTHER PUBLICATIONS

Freeman, "Pancreatic Stents for Prevention of Post-Endoscopic Retrograde Cholangiopancreatography Pancreatitis," *Clinical Gastroenterology and Hepatology*, Nov. 2007; 5(11): 1354-1365.

Katsinelos et al., "Migration of Plastic Biliary Stents and Endoscopic Retrieval: An Experience of Three Referral Centers," *Surg. Laparosc. Endosc. Percutan. Tech.*, Jun. 2009; 19(3): 217-221.

(Continued)

*Primary Examiner* — Elizabeth Houston

(74) *Attorney, Agent, or Firm* — Mueting, Raasch & Gebhardt, P.A.

(57) ABSTRACT

Stents, kits and methods of using the stents are described herein. The stents may include one or more features that assist in removal and/or retrieval of the stent after deployment.

14 Claims, 6 Drawing Sheets

(56) References Cited

OTHER PUBLICATIONS

Sakai et al., "Cholangiopancreatography troubleshooting: the usefulness of endoscopic retrieval of migrated biliary and pancreatic stents," *Hepatobiliary Pancreat. Dis. Int.*, Dec. 15, 2009; 8(6): 632-637.

Siepmann et al., "Polymer blends for controlled release coatings" *Journal of Controlled Release*, Jan. 4, 2008; 125(1): 1-15. Available online Oct. 13, 2007.

\* cited by examiner

REMOVABLE AND/OR RETRIEVABLE STENTS AND KITS

RELATED APPLICATION

This application claims the benefit under 35 U.S.C. §119 of U.S. Provisional Application Ser. No. 61/317,406, filed Mar. 25, 2010, entitled REMOVABLE AND/OR RETRIEVABLE STENTS AND KITS, which is incorporated herein by reference in its entirety.

Stents that include one or more features to assist in removal and/or retrieval of a stent after deployment are described herein. Kits and methods associated with such stents are also described herein.

Although the stents described herein may be used for biliary and/or pancreatic ducts, the stents may also be used in many different body lumens, such as, e.g., the ureter, esophagus, etc.

The following patent documents describe devices, systems and methods related to the retrieval and/or removal of stents: U.S. Pat. No. 5,334,208 (Soehendra et al.); U.S. Pub. No. US 2007/0129719 (Kendale et al.); U.S. Pub. No. US 2005/0131515 (Cully et al.); U.S. Pub. No. US 2006/0190075 (Jordan et al.); U.S. Pub. No. US 2006/0276887 (Brady et al.); and U.S. Pub. No. US 2009/0093822 (Ducharme).

SUMMARY

The stents described herein include one or more features that can assist in spontaneous migration of the stent from a deployed location and/or that can be used to retrieve a stent after deployment.

Among the different illustrative embodiments of stents described herein, some embodiments include removal elements that are provided to assist in migration or dislodgement of the stent out of a deployment location either at a selected time or over a selected period of time.

In those embodiments that are designed to prophylactically and spontaneously dislodge or migrate out of their deployed location at a selected time, the removal feature may be capable of a relatively rapid increase in size and/or mass of the removal element (e.g., an increase in size and/or mass over a period of 24 hours or less of 50% or more, 100% or more, 150% or more, or 200% or more). In some of the embodiments designed for migration/dislodgement at a selected time and in which the stent is deployed in the digestive system of a mammal, the increase in size and/or mass may be the facilitated by the ingestion of selected composition that is capable of effecting the increase in size and/or mass of the removal element. Some illustrative examples of potentially useful compositions are described herein.

In those embodiments that are designed to prophylactically and spontaneously dislodge or migrate out of their deployed location after a selected period of time, the removal element may be increase in size and/or mass over a period of time at a gradual rate that may, e.g., extend over 2 days or more, 3 days or more, 1 week or more, 2 weeks or more, 3 weeks or more, etc. depending on the characteristics imparted to the removal element. In other embodiments, the removal element may include a self-expanding structure that is initially constrained but that, upon removal of the constraint, expands in size to facilitate removal of the attached stent from its deployed location. That constraint may be provided in the form of a degradable material that weakens over time after being implanted in a deployed location (e.g., wax, biodegradable materials, etc.) such that the constraint eventually fails, thereby allowing the removal element to expand from its constrained configuration. After expansion, the removal element is then preferably capable of promoting prophylactic and spontaneous dislodgement or migration of the stent.

Some embodiments of the stents described herein include one or more removal elements that are provided to assist with retrieval of the attached stent from its deployed location using one or more retrieval apparatus that are advanced to the deployment location when the stent is to be removed.

In a first aspect, some embodiments of an implantable stent as described herein include: a body comprising a first end and a second end, wherein a lumen extends through the body from the first end to the second end; and a removal element fixedly attached to the stent and extending away from the first end of the body, wherein the removal element comprises a first configuration in which the removal element has a first size and/or mass and a second configuration in which the removal element has a second size and/or mass, wherein the first size is smaller than the second size and/or the first mass is smaller than the second mass.

In some embodiments of stents of the first aspect, the removal element comprises a porous body comprising pores opening on an exterior surface of the porous body.

In some embodiments of stents of the first aspect, the removal element comprises an electrically charged body having a net positive or a net negative electric charge.

In some embodiments of stents of the first aspect, the removal element comprises a hydrophilic material capable of increasing the size and/or mass of the removal element.

In some embodiments of stents of the first aspect, the stent is provided in a kit that includes a configuration switching composition comprises an ingestible material suitable for introduction into the digestive system of a mammal, wherein the configuration switching composition interacts with the removal element to cause the removal element to move from the first configuration to the second configuration. In some embodiments, the removal element of the stent in the kit comprises a porous body comprising pores opening on an exterior surface of the porous body; and wherein the configuration switching composition comprises particles sized to enter the pores on the exterior surface of the porous body. In some embodiments, the removal element of the stent in the kit comprises an electrically charged body having a net positive or a net negative electric charge; and wherein the configuration switching composition comprises electrically charged material having a net positive or negative electric charge that is opposite of the electrical charge of the body such that at least a portion of the electrically charged material is electrically retained on and/or in the electrically charged body.

In a second aspect, some embodiments of an implantable stent as described herein include: a body comprising a first end and a second end, wherein a lumen extends through the body from the first end to the second end; and a removal element fixedly attached to the stent and extending away from the first end of the body, wherein the removal element comprises a first configuration in which the removal element has a first size and a second configuration in which the removal element has a second size, wherein the first size is smaller than the second size, and wherein the removal element comprises a self-expanding structure that is constrained in the first configuration; and further wherein the removal element is not constrained in the second configuration.

In some embodiments of stents of the second aspect, the removal element is constrained in the first configuration by a constraint element comprising enteric coating material.

In some embodiments of stents of the second aspect, the removal element is constrained in the first configuration by a constraint element comprising biodegradable material.

In a third aspect, some embodiments of an implantable stent as described herein include: a body comprising a first end and a second end, wherein a lumen extends through the body from the first end to the second end; and a removal element comprising a flexible tether attached to the body, wherein the removal element further comprises a bead attached to the flexible tether. In some embodiments, the removal element comprises a plurality of beads attached to the tether, wherein the beads are spaced apart from each other along the flexible tether.

In a fourth aspect, some embodiments of an implantable stent as described herein include: a body comprising a first end and a second end, wherein a lumen extends through the body from the first end to the second end; and a removal element comprising a mesh sleeve attached to the body of the stent.

In some embodiments of stents of the fourth aspect, the stent is provided in a kit that also includes a retrieval apparatus comprising a pair of sickle-shaped arms pivotally mounted on a distal end of a delivery shaft, wherein the arms comprise an open configuration in which the sickle-shaped arms are located on opposite sides of a longitudinal axis extending through the delivery shaft such that the sickle-shaped arms do not overlap each other and a closed configuration in which the sickle-shaped arms cross over the longitudinal axis such that the sickle-shaped arms do overlap each other.

In some embodiments of stents of the fourth aspect, the stent is provided in a kit that also includes a retrieval apparatus comprising a hook element mounted on a distal end of a delivery shaft, wherein the delivery shaft is located in a delivery sheath, and further wherein the hook element rotates about a longitudinal axis extending through the sheath. In some embodiments, the hook element comprises two hooks.

In a fifth aspect, some embodiments of an implantable stent as described herein include: a body comprising a first end and a second end, wherein a lumen extends through the body from the first end to the second end; and a removal element comprising a bar attached to the body.

In some embodiments of stents of the fifth aspect, the bar of the removal element is located within the lumen such that the bar spans the lumen in a direction transverse to a longitudinal axis extending along the lumen between the first end and the second end of the body.

In some embodiments of stents of the fifth aspect, the removal element comprises a plurality of bars, wherein each bar of the plurality of bars is located within the lumen such that the bar spans the lumen in a direction transverse to a longitudinal axis extending along the lumen between the first end and the second end of the body.

In a sixth aspect, some embodiments of an implantable stent as described herein include: a body that comprises a first end and a second end, wherein a lumen extends through the body from the first end to the second end, and wherein the body comprises a pair of openings located on opposite sides of the body proximate the first end of the body.

In some embodiments of stents of the sixth aspect, the body comprises a substantially solid tubular structure.

In some embodiments of stents of the sixth aspect, the body comprises a circular cylindrical body and the pair of openings are located along a diameter of the body.

In some embodiments of stents of the sixth aspect, the body comprises two or more pairs of openings located on opposite sides of the body proximate the first end of the body. In some embodiments, the pairs of openings are spaced apart from each other along a longitudinal axis extending through the lumen between the first end and the second end of the body.

In some embodiments, stents of the sixth aspect are provided in a kit that also includes a retrieval apparatus, wherein the retrieval apparatus comprises a an expandable element located at the distal end of a retrieval shaft, wherein the expandable element comprises a first insertion configuration in which the retrieval apparatus can be passed through the pair of openings and a second expanded configuration in which the retrieval element is expanded such that it cannot pass through the pair of openings.

In some embodiments of stents of a seventh aspect, the stent comprises a body comprising a first end and a second end, wherein a lumen extends through the body from the first end to the second end; and a removal tab attached to the first end of the body, wherein the removal tab extends past the first end of the body.

In some embodiments of stents of the seventh aspect, the removal tab comprises a portion of the body of the stent, such that the body of the stent comprises an opening corresponding in size and shape to the removal tab.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a removal element may be used to refer to one, two, three or more removal elements.

The term "and/or" means one or all of the listed elements or a combination of any two or more of the listed elements.

The above summary is not intended to describe each embodiment or every implementation of the present invention. Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

Figure 1:
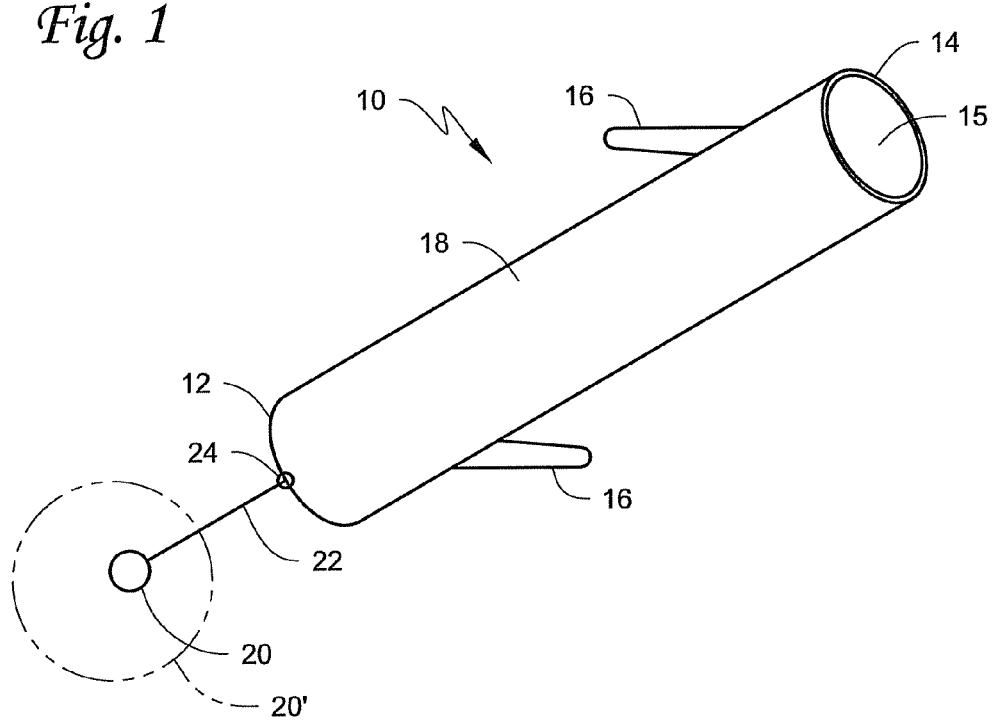
FIG. 1 is a perspective view of one embodiment of a stent as described herein.

In the following description of illustrative embodiments, reference is made to the accompanying figures of the drawing which form a part hereof, and in which are shown, by way of illustration, specific embodiments of stents and stent systems. It is to be understood that other embodiments may be utilized and structural changes may be made without departing from the scope of the present invention.

The stents described herein may be manufactured using a wide variety of materials. Reference may be had to the one or more of the following patents for further details regarding potentially suitable techniques for construction, manufacturing, and/or deployment of stents: U.S. Pat. Nos. 4,733,665; 4,739,762; 5,195,984; 5,725,572; 5,735,871; 5,755,781; 5,853,419; 5,861,027; 6,007,573; 6,059,810; 6,099,561; 6,200,337; and 6,206,916; etc. The materials used to construct the stents described herein are preferably biocompatible materials. As used herein, "biocompatible materials" are materials that can be implanted within a living body for an extended period of time, e.g., weeks, months and/or years.

One illustrative embodiment of a stent as described herein is depicted in the perspective view of FIG. 1. The stent includes a body member 10 that has a wall 18 extending between a first end 12 and a second end 14. The stent includes a lumen 15 that extends through the body 10 from the first end 12 to the second end 14. The lumen 15 is defined by the wall 18 of the stent body 10. The stent also includes features 16 protruding from wall 18 that may assist in retaining the stent in position when deployed within a body lumen.

The stent of FIG. 1 also includes a removal element 20 attached to the body 10 of the stent. In some embodiments, the removal element 20 may be fixedly attached to the body 10, where the term "fixedly attached" means that separation of the removal from the body 10 of the stent would require destruction (e.g., cutting, tearing, rupturing, etc.) some component in a manner that is irreversible.

In some embodiments, the removal element 20 may be attached to the body 10 by a tether 22 such that the removal element 20 and tether 22 extend away from the first end 12 of the body 10. The tether 22 may, for example, be attached to the body 10 at location 24 located on the or near the first end 12 of the body 10. In some embodiments, the tether 22 may, for example, be attached to the body 10 at more than one location on or near the first end 12 of the body 10. The tether 22 may, e.g., preferably be formed of a flexible cable, line, string, suture material, wire, etc.

"Flexible" as used herein to describe tethers in connection with the various embodiments means that the tether is deflected due to forces applied to the removal element by materials passing through the body lumen or cavity in which the removal element is located. For example, the passage of fluids and other materials through the intestine or may generate forces on the removal element that bend or otherwise deflect the flexible tether attaching the removal element to the stent body.

In some embodiments, the removal element 20 may have a first configuration in which the removal element 20 has a first size and/or mass (where the removal element 20 is depicted in a first size by the solid lines in FIG. 1). The removal element 20 may also have a second configuration in which the removal element 20 has a second size and/or mass (where the removal element 20 is depicted in the second size by reference number 20' in FIG. 1). In general, the first size of the removal element 20 is smaller than the second size and/or the first mass is smaller than the second mass.

The increase in size and/or mass of the removal element 20/20' from the first configuration to the second configuration may, if the stent is used in a bile or pancreatic duct, assist in removal of the stent in the distal direction from the duct by the forces applied to the removal element by the passage of food and/or duodenal peristalsis. The increase in size and/or weight may preferably occur at a selected time and/or over a selected time period. In some embodiments, the selected time period may be, e.g., 2 days or more, 3 days or more, 1 week or more, 2 weeks or more, 3 weeks or more, etc. In some embodiments, the selected time at which the increase in size and/or weight occurs may be selected by delivering a selected material into the body lumen in which the removal element is located. For example, electrically charged materials, magnetic materials, materials that activate or dissolve constraining material that constrains the size of removal element such that the removal element can increase in size and/or weight may all be used to provide control led removal at a selected time.

In various embodiments, the removal element 20/20' may be in the form of a porous body that may, e.g., include pores opening on the exterior surface of the porous body. Examples of porous bodies that may be used in the removal element 20 may include, e.g., foam materials, sponge materials, mesh materials, etc. In the case of a porous body, the increase in size and/or weight of the removal element 20/20' may occur over a selected period of time as material enters the porous body. In some embodiments, the material entering the porous body may be aqueous liquids present in the body.

In some embodiments, the removal element 20 may include hydrophilic material that absorbs and/or adsorbs aqueous liquids to increase the size and/or mass of the removal element 20/20'.

In some embodiments, the stents that include a removal element as described in connection with FIG. 1 may be provided in a kit that also includes a configuration switching composition that can be used to switch the removal element from the first configuration to the second configuration. The configuration switching composition may be in the form of ingestible material suitable for introduction into the digestive system of a mammal, wherein the configuration switching composition interacts with the removal element 20 to cause the removal element 20 to move from the first configuration to the second configuration.

In those embodiments in which the removal element 20 is in the form of a porous body as described herein, the configuration switching composition may preferably include particles sized to enter the pores on the exterior surface of the porous body. The particles sized to enter the pores may, in some embodiments, be provided in a form that can be ingested by a person, e.g., they may be contained in a composition, suspension, liquid, capsule, tablet, embedded in food, etc.

In those embodiments in which the removal element 20 is in the form of an electrically charged body having a net positive or a net negative electric charge, the configuration switching composition may preferably include electrically charged material having a net positive or negative electric charge that is opposite of the electrical charge of the body such that at least a portion of the electrically charged material is electrically retained on and/or in the electrically charged body. The electrically charged material may, in some embodiments, be provided in a form that can be ingested by a person, e.g., they may be contained in a composition, suspension, liquid, capsule, tablet, embedded in food, etc.

In still other embodiments, the configuration switching composition may include magnetic material and the removal element 20 may be magnetized such that the magnetic material in the configuration switching composition is magnetically attracted to the removal element 20 to increase its size and/or mass. The magnetic material may, in some embodiments, be provided in a form that can be ingested by a person, e.g., they may be contained in a composition, suspension, liquid, capsule, tablet, embedded in food, etc.

Figure 2A:
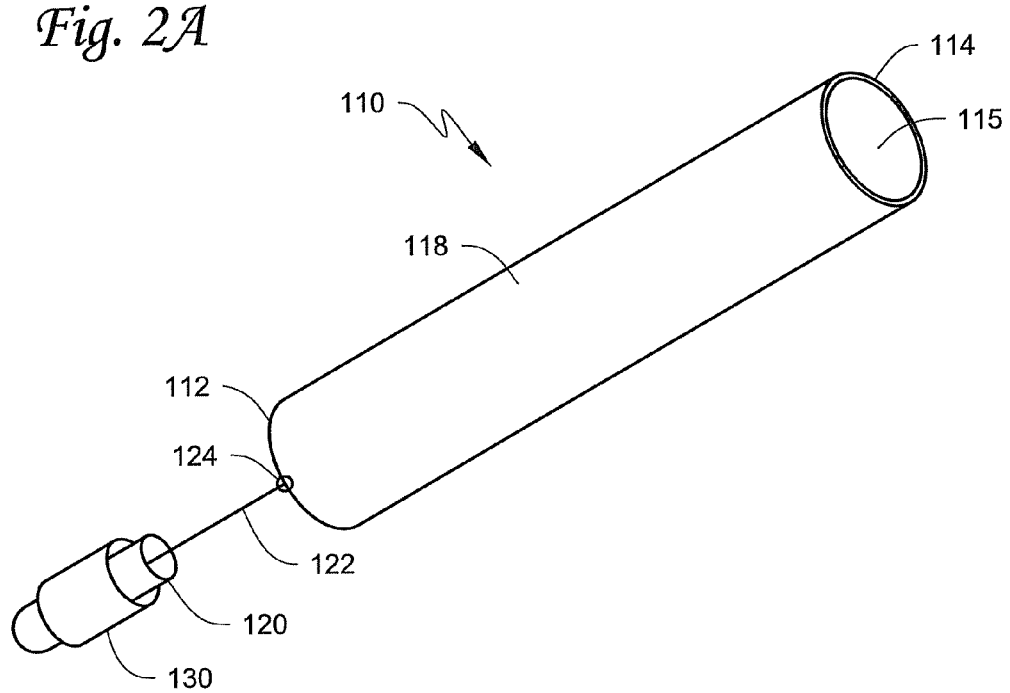
FIG. 2A is a perspective view of another embodiment of a stent as described herein.
Figure 2B:
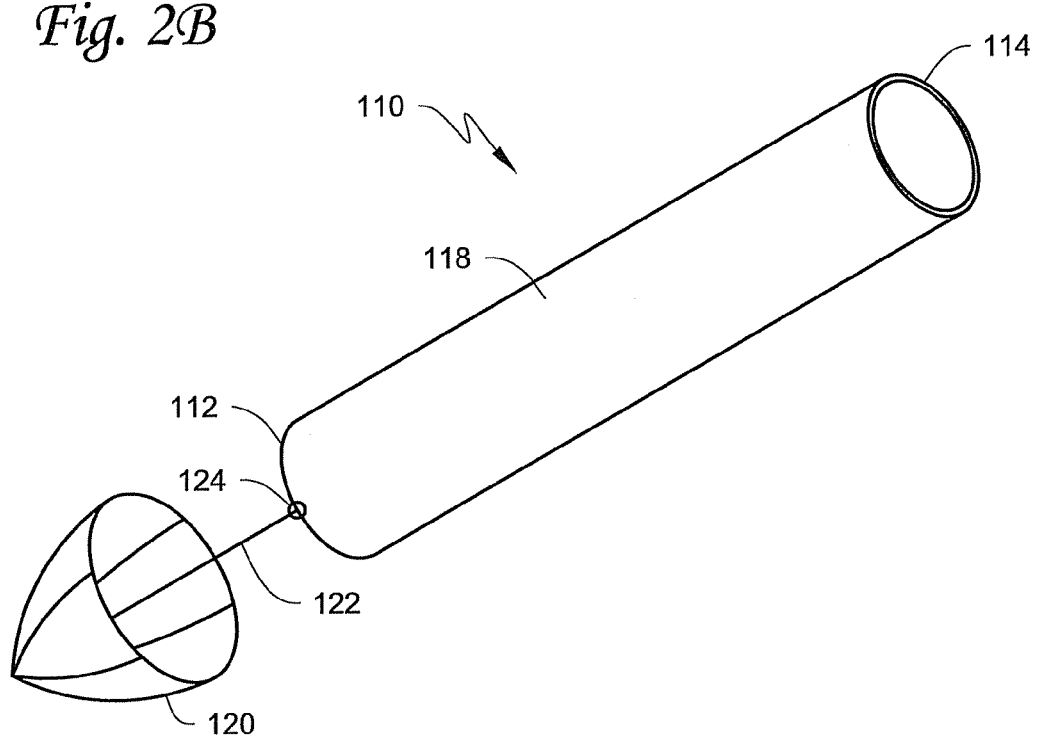
FIG. 2B is a perspective view of the stent of FIG. 2A after deployment of the removal element.

Another embodiment of a stent as described herein is depicted in FIGS. 2A and 2B. The stent includes a body member 110 that has a wall 118 extending between a first end 12 and a second end 14. The stent includes a lumen 15 that extends through the body 10 from the first end 12 to the second end 14. The lumen 15 is defined by the wall 18 of the stent body 10.

The stent of FIG. 2A also includes a removal element 120 attached to the body 110 of the stent. In some embodiments, the removal element 120 may be fixedly attached to the body 110. In some embodiments, the removal element 120 may be attached to the body 110 by a tether 122 such that the removal element 120 and tether 122 extend away from the first end 112 of the body 110. The tether 122 may, for example, be attached to the body 110 at location 124 located on the or near the first end 112 of the body 110. In some embodiments, the tether 122 may, for example, be attached to the body 110 at more than one location on or near the first end 112 of the body 110. The tether 122 may, e.g., preferably be formed of a flexible cable, line, string, suture material, wire, spring, etc.

In some embodiments, the removal element 120 may have a first configuration in which the removal element 120 has a first size as depicted in FIG. 2A and a second configuration in which the removal element 120 has a second size as depicted in FIG. 2B. In general, the first size of the removal element 120 is smaller than the second size.

The increase in size of the removal element 120 from the first configuration to the second configuration may, if the stent is used in a bile or pancreatic duct, assist in removal of the stent in the distal direction from the duct by the forces applied to the removal element 120 by the passage of food and/or duodenal peristalsis. The increase in size may preferably occur at a selected time and/or over a selected time period. In some embodiments, the selected time period may be, e.g., 2 days or more, 3 days or more, 1 week or more, 2 weeks or more, 3 weeks or more, etc.

Control over the change in the size of the removal element 120 from the first configuration (FIG. 2A) to the second configuration (FIG. 2B) may be accomplished, in some embodiments, by constraining the removal element 120 in the first configuration by a constraint element 130 that may be in the form of material that, when first deployed in the body, is sufficiently strong to constrain the removal element 120 in the first configuration as depicted in FIG. 2A. After introduction into the body, however, the material in constraint element 130 may degrade such that the removal element 120 can expand to a larger size (see, e.g., FIG. 2B).

The materials used to form the constraint element may include, e.g., biodegradable materials, etc. Examples of some potentially suitable biodegradable materials may include wax, ethylcellulose, dried and/or solid plant or other food-based material that could, in some embodiments, be digested, etc. In some embodiments, the constraint element could include materials used for enteric coatings (i.e., coatings designed to break down in the intestine). Examples of some enteric coating materials that could potentially be used may include, e.g., fatty acids, waxes, shellac, plastics, plant materials, etc. Other potentially useful enteric coating materials may include, e.g., Cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate, stearic acid, etc. Other biodegradable materials that may potentially be used in the constraint element may include some of the materials described in Siepmann et al., *Polymer blends for controlled release coatings*, Journal of Controlled Release, Vol. 125 (2008), pages 1-15.

Although the removal element 120 depicted in FIG. 2B is in one form of a parachute-like shape, the removal elements used in connection with the stents depicted and described in FIGS. 2A and 2B may take any suitable shape, in other words, the shape of the removal element 120 depicted in FIG. 2B is exemplary in nature only and other shapes may be used.

Figure 3:
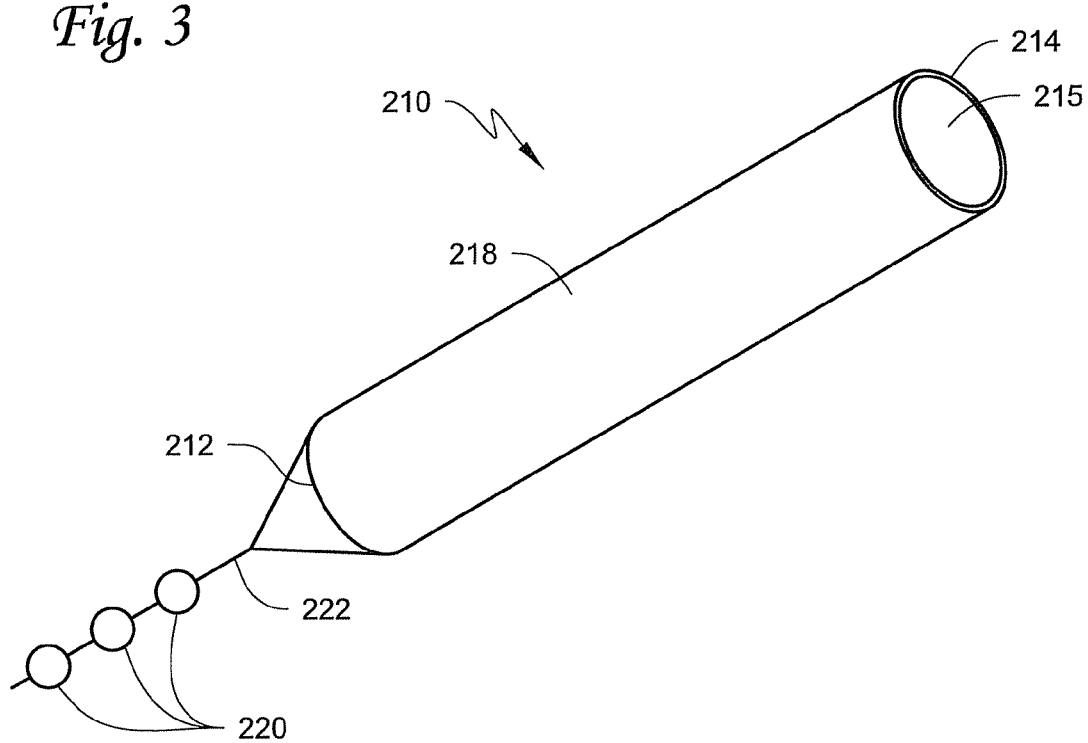
FIG. 3 is a perspective view of another embodiment of a stent as described herein.

Another embodiment of a stent as described herein is depicted in FIG. 3. The stent includes a body member 210 that has a wall 218 extending between a first end 212 and a second end 214. The stent includes a lumen 215 that extends through the body 210 from the first end 212 to the second end 214. The lumen 215 is defined by the wall 218 of the stent body 210.

The stent of FIG. 3 also includes removal elements 220 attached to the body 210 of the stent. In some embodiments, the removal elements 220 may be fixedly attached to the body 210. In some embodiments, the removal elements 220 may be attached to the body 210 by a tether 222 such that the removal elements 220 and tether 222 extend away from the first end 212 of the body 210. The tether 222 may, for example, be attached to the body 210 at one or more locations located on the or near the first end 212 of the body 210. The tether 222 may preferably be formed of a flexible cable, line, string, etc.

Although three removal elements 220 may be depicted in FIG. 3, the stent may include only one, two or more than three removal elements which may be attached to one, two or three tethers. In embodiments that include two or more beads 220 attached along a tether 222, the beads 220 may preferably be spaced apart along the tether by a distance that may facilitate their capture, e.g., by the diameter of the bead 220, etc.

The removal elements 220 may be in the foam of beads attached to the tether 222. The beads 220 may be sized and shaped to facilitate their capture by, e.g., a retrieval device that can be introduced endoscopically or by any other suitable technique. In some embodiments, the beads may be metallic and/or magnetic to further assist in their capture.

Figure 4:
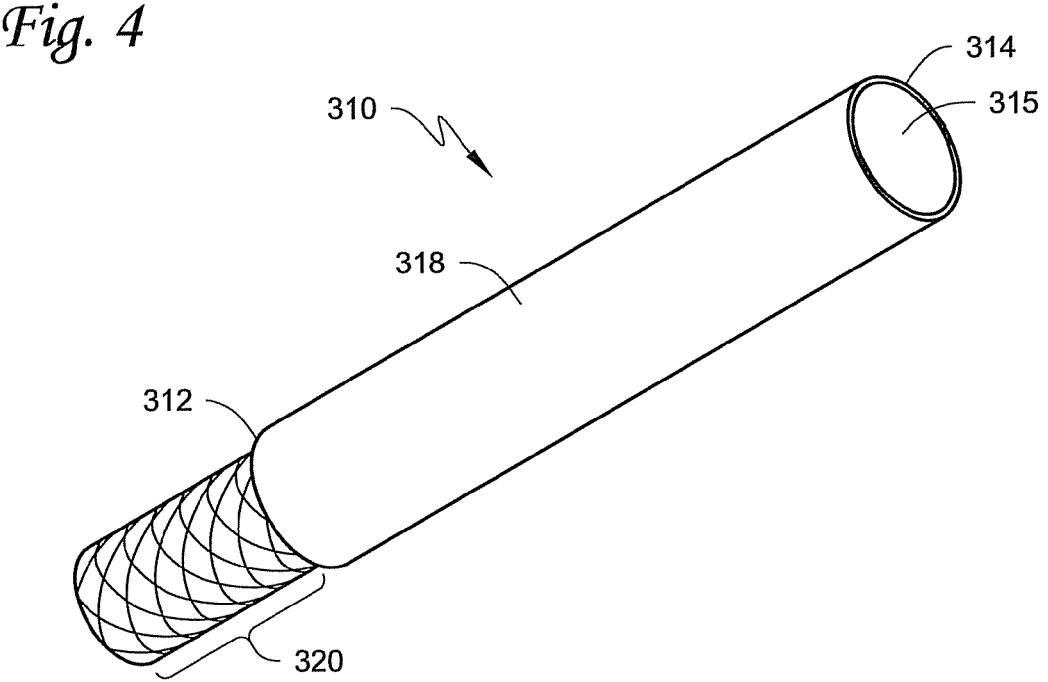
FIG. 4 is a perspective view of another embodiment of a stent as described herein.

Still another embodiment of a stent as described herein is depicted in FIG. 4. The stent includes a body member 310 that has a wall 318 extending between a first end 312 and a second end 314. The stent includes a lumen 315 that extends through the body 310 from the first end 312 to the second end 314. The lumen 315 is defined by the wall 318 of the stent body 310.

The stent of FIG. 4 also includes a removal element 320 attached to the body 310 of the stent. The removal element 320 is in the form of a mesh sleeve attached to the body 310 of the stent. The mesh sleeve may preferably be in the form of a flexible, open weave element that can be trimmed to a selected length at the time of deployment. The open structure of the mesh sleeve preferably does not undesirably obstruct flow past the sleeve.

Figure 5:
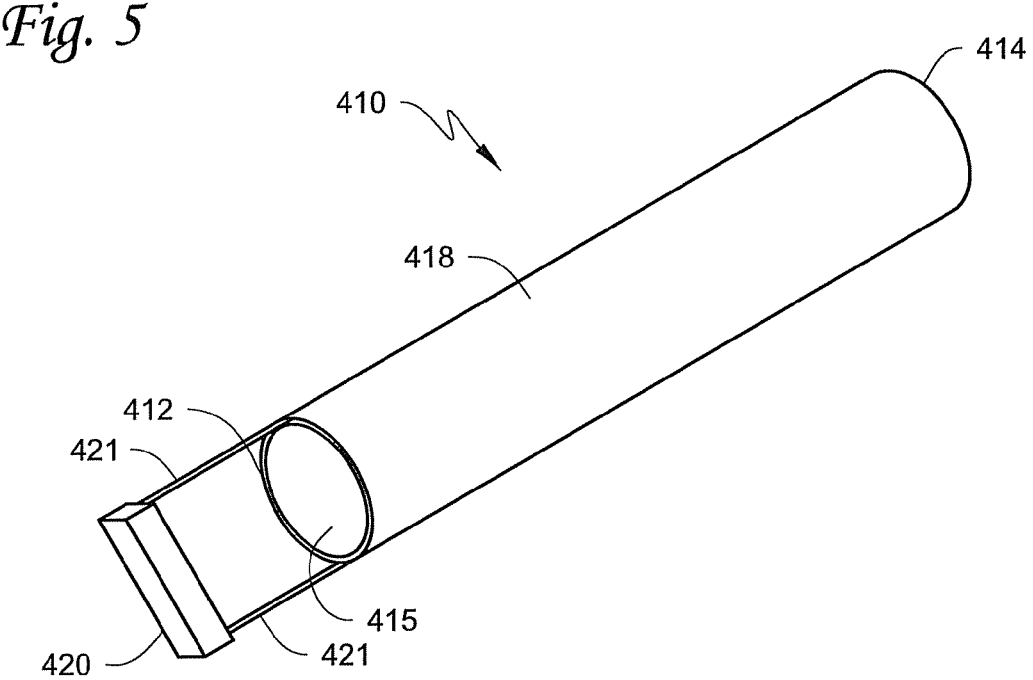
FIG. 5 is a perspective view of another embodiment of a stent as described herein.

Yet another embodiment of a stent as described herein is depicted in FIG. 5. The stent includes a body member 410 that has a wall 418 extending between a first end 412 and a second end 414. The stent includes a lumen 415 that extends through the body 410 from the first end 412 to the second end 414. The lumen 415 is defined by the wall 418 of the stent body 410.

The stent of FIG. 5 also includes a removal element 420 attached to the body 410 of the stent. The removal element 420 is in the form of a bar attached to the body of the stent. The bar 420 can preferably be grasped by a variety of implements to facilitate removal of the stent from a body lumen. The bar may, in some embodiments, be magnetic to facilitate its capture. The bar 420 may be attached to the first end 412 of the body 410 by struts 421 that keep the bare 420 at a selected distance from the end 412 of the body 410.

Figure 6:
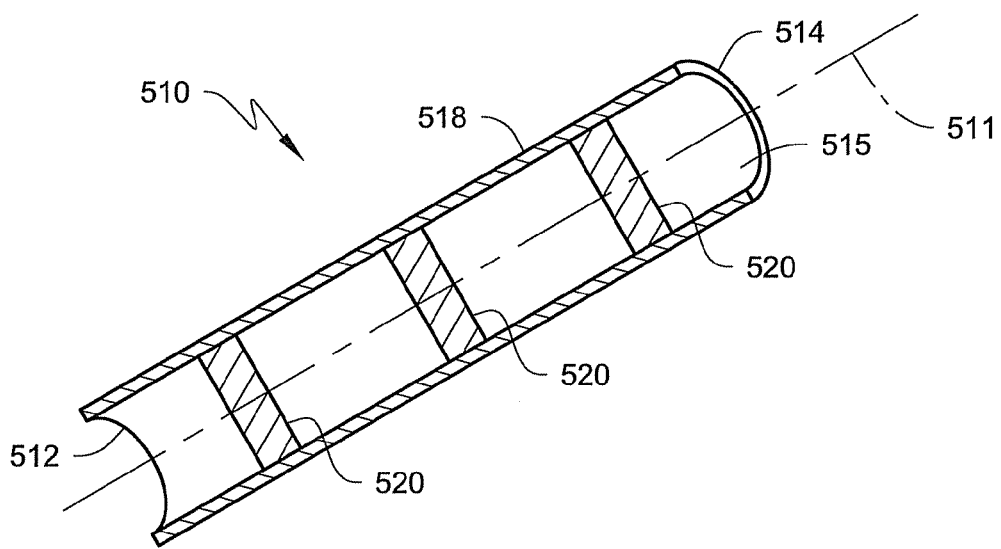
FIG. 6 is a cross-sectional view of another embodiment of a stent as described herein.

Yet another embodiment of a stent as described herein is depicted in a cross-sectional view in FIG. 6. The stent includes a body member 510 that has a wall 518 extending between a first end 512 and a second end 514. The stent includes a lumen 515 that extends through the body 510 from the first end 512 to the second end 514. The lumen 515 is defined by the wall 518 of the stent body 510.

The stent of FIG. 6 includes a removal element in the form of a plurality of bars 520 that are located within the lumen 515 of the body 510. The bars 520 may preferably span the lumen 515 in a direction transverse to the longitudinal axis 511 extending through the lumen 515 between the first end 512 and the second end 514 of the body 510.

Removal of the stent depicted in FIG. 6 can be accomplished by inserting a retrieval tool into the lumen 515 where it can engage one or more of the bars 520 to provide the required force to remove the stent from a body lumen in which it is located.

Figure 7A:
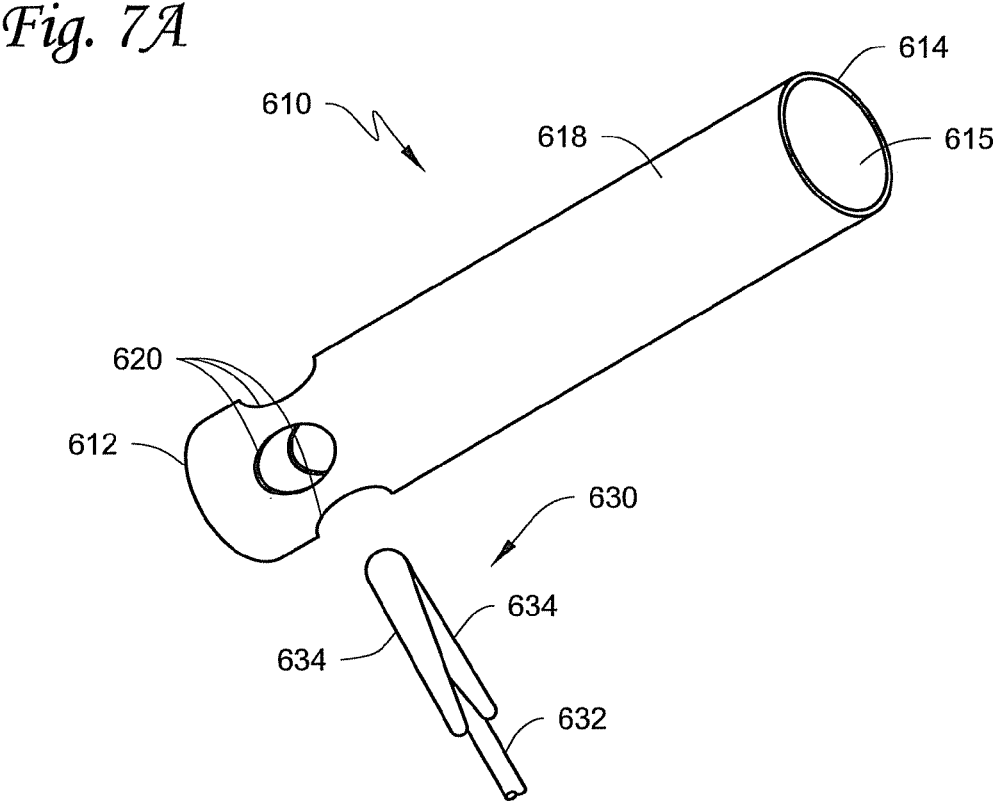
FIG. 7A is a perspective view of another embodiment of a stent and a retrieval apparatus as described herein.
Figure 7B:
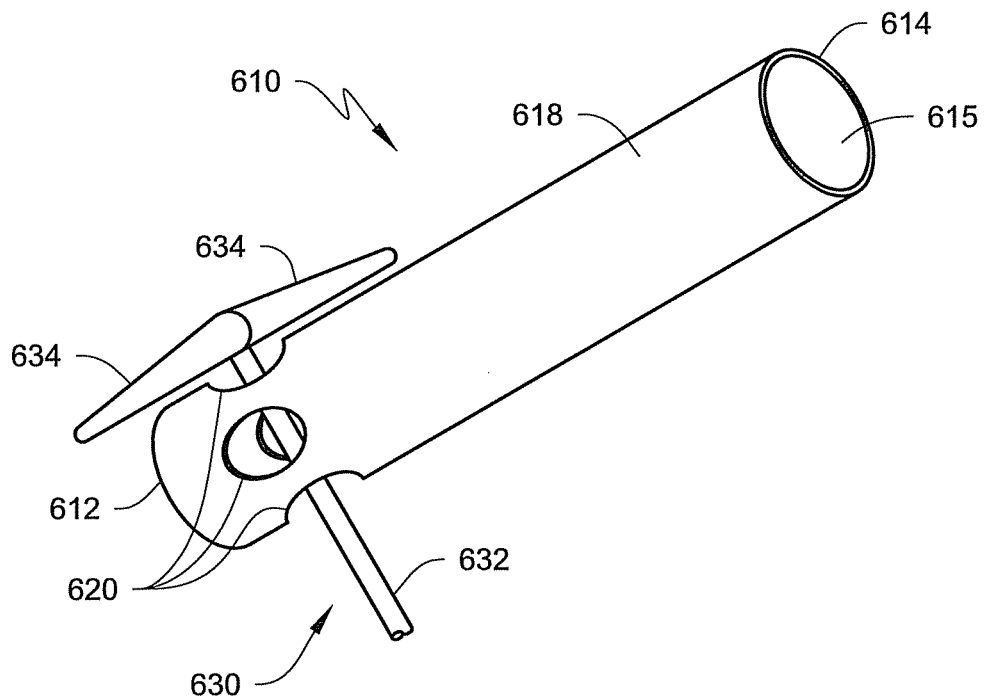
FIG. 7B is a perspective view of the stent and retrieval apparatus of FIG. 7A after passage of the retrieval apparatus through openings in the stent.

Yet another embodiment of a stent as described herein is depicted in FIGS. 7A and 7B in connection with a retrieval apparatus. The stent includes a body 610 extending between a first end 612 and a second end 614. The stent includes a lumen 615 that extends through the body 610 from the first end 612 to the second end 614. The lumen 615 is defined by the wall 618 of the stent body 610.

The stent of FIGS. 7A and 7B includes two pairs of openings 620 in the wall 618 of the stent body 610, wherein each pair of openings 620 is located on opposite sides of the stent body 610. In some embodiments, only on pair of openings 620 may be provided, while in other embodiments three or more pairs of openings 620 may be provided. The openings 620 may preferably be located proximate the first end 612 of the body 610. In some embodiments, the body 610 may preferably be in the form of a solid tubular structure except for the openings 620. In some embodiments, the body 610 may be in the form of a circular cylindrical body with the pair or pairs of openings located across from each other on a diameter defined by the circular cylindrical body.

FIGS. 7A and 7B also depict one embodiment of a retrieval apparatus 630 that may be used in connection with the depicted stent. The depicted retrieval apparatus 630 includes an expandable element located at the distal end of a retrieval shaft 632. The expandable element has a first insertion configuration in which the retrieval apparatus 630 can be advanced through the pair of openings 620 and a second expanded configuration in which the retrieval element 630 is expanded such that it cannot pass through the openings 620 (in the form of, e.g., a toggle bolt). The depicted retrieval apparatus 630 includes a pair of arms 634 that are generally aligned with the shaft 632 in the first insertion configuration (see, e.g., FIG. 7A). The pair of arms 634 are then extended away from the shaft 632 after the retrieval apparatus 630 has been advanced through the openings 620 (see, e.g., FIG. 7B). The stent can then be removed using the retrieval apparatus 630 which cannot move back through the openings 620 because of the expanded arms 634.

Figure 8:
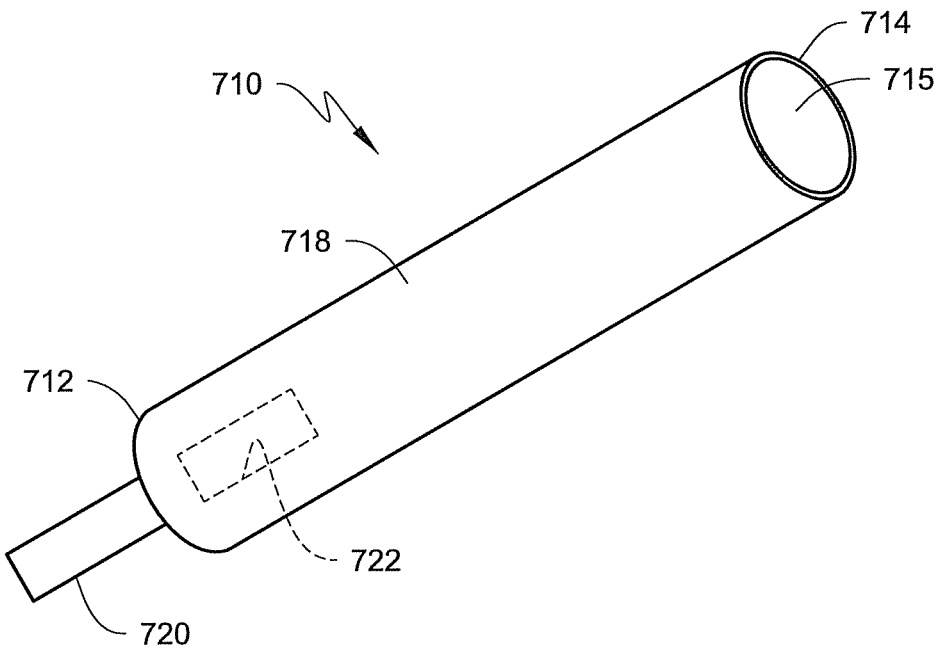
FIG. 8 is a perspective view of another embodiment of a stent as described herein.

Yet another embodiment of a stent as described herein is depicted in FIG. 8. The stent includes a body 710 extending between a first end 712 and a second end 714. The stent includes a lumen 715 that extends through the body 710 from the first end 712 to the second end 714. The lumen 715 is defined by the wall 718 of the stent body 710.

The stent of FIG. 8 includes a removal tab 720 attached to the first end 712 of the body 710, wherein the removal tab 720 extends past the first end 712 of the body 710. The removal tab 720 can preferably be grasped by a variety of implements to facilitate removal of the stent from a body lumen. In some embodiments, the removal tab 720 may be in the form of a portion of the body 710 of the stent, such that the body 710 of the stent comprises an opening (see, e.g., feature 722 in broken lines in FIG. 8) that corresponds in size and shape to the removal tab 720. In other embodiments, the removal tab may be provided as a separate element that is attached to the body of the stent by, e.g., welding, adhesives, etc.

Figure 9A:
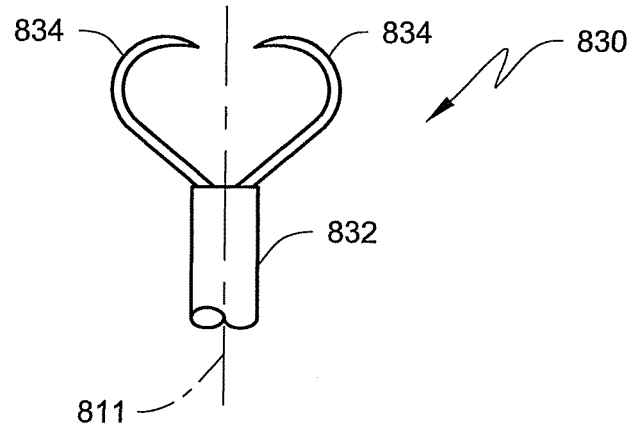
FIG. 9A depicts a retrieval apparatus in the form of a pair of sickle-shaped arms on a delivery shaft, with the arms in an open configuration.
Figure 9B:
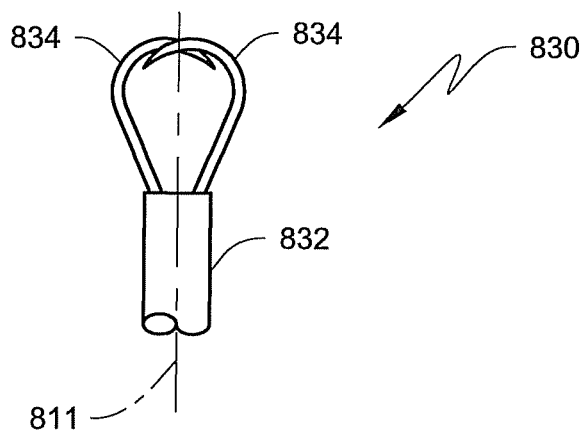
FIG. 9B depicts the retrieval apparatus of FIG. 9B with the arms in a closed configuration.

One embodiment of a retrieval apparatus that may be used with some embodiments of the stents described herein is depicted in FIGS. 9A and 9B. The retrieval apparatus 830 includes a pair of sickle-shaped arms 834 that are pivotally attached to the end of a delivery shaft 832. As seen in the view of FIG. 9A, the arms 834 have an open configuration in which the sickle-shaped arms 834 are located on opposite sides of a longitudinal axis 811 extending along the delivery shaft 832 such that the sickle-shaped arms 834 do not overlap each other. The arms 834 can be rotated into a closed configuration as depicted in FIG. 9B in which the sickle-shaped arms 834 cross over the longitudinal axis 811 such that the sickle-shaped arms 834 do overlap each other. One potential advantage of such an embodiment is that the retrieval element 830 can have a relatively low profile that can allow retraction of the retrieval element 830 into, e.g., the channel of an endoscope or other delivery device.

Figure 10:
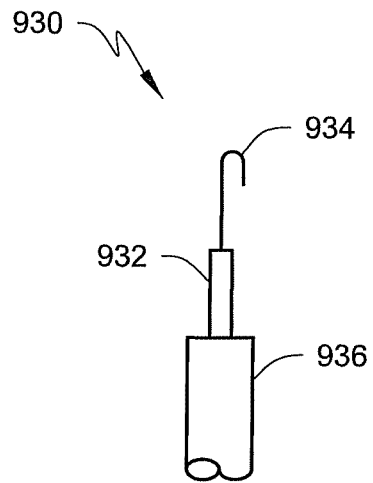
FIG. 10 depicts another embodiment of a retrieval apparatus in the form of a hook element.

Another embodiment of a retrieval apparatus 930 is depicted in FIG. 10 in the form of a hook element 934 mounted on a distal end of a delivery shaft 932. The delivery shaft 932 may preferably be located within a sheath 936 and movable therein such that the hook element 934 can be extended out of and/or retracted into the sheath 936. In some embodiments, the hook element preferably rotates about a longitudinal axis extending through the sheath 936 to change the direction of the hook element 934 independently of the sheath 936.

Figure 11:
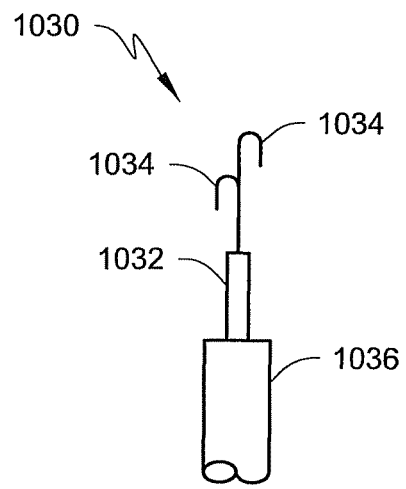
FIG. 11 depicts another embodiment of a retrieval apparatus in the form of a hook element that includes two hooks.

Yet another embodiment of a retrieval apparatus 1030 is depicted in FIG. 11 and includes two hook elements 1034 mounted on the distal end of a delivery shaft 1032. The delivery shaft 1032 may preferably be located within a sheath 1036 and movable therein such that the hook elements 1034 can be extended out of and/or retracted into the sheath 1036. In some embodiments, the hook elements and the delivery shaft 1032 preferably rotate about a longitudinal axis extending through the sheath 1036 to change the direction of the hook elements 1034 independently of the sheath 1036. The hook elements 1034 may preferably be offset rotationally about the delivery shaft 1032.

The complete disclosure of the patents, patent documents, and publications cited in herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An implantable stent comprising:
a body comprising a first end and a second end, wherein a lumen extends through the body from the first end to the second end; and
a removal element fixedly attached to the body and extending away from the first end of the body, wherein the removal element comprises a first configuration in which the removal element has a first size and a second configuration in which the removal element has a second size, wherein the first size is smaller than the second size, and wherein the removal element comprises a self-expanding structure that is constrained in the first configuration; and further wherein the removal element is not constrained in the second configuration;
wherein the removal element increases from the first size to the second size over a selected period of time comprising two days or more after introduction into a body.

2. A stent according to claim 1, wherein the removal element is constrained in the first configuration by a constraint element comprising enteric coating material.

3. A stent according to claim 1, wherein the removal element is constrained in the first configuration by a constraint element comprising biodegradable material.

4. A stent according to claim 1, wherein the removal element is attached to the stent by a flexible tether.

5. A stent according to claim 1, wherein the removal element comprises a parachute-like shape in the second configuration.

6. A stent according to claim 1, wherein the removal element is attached to the stent by a flexible tether, and wherein the removal element comprises a parachute-like shape in the second configuration.

7. An implantable stent comprising:
a body comprising a first end and a second end, wherein a lumen extends through the body from the first end to the second end; and
a removal element fixedly attached to the body by a flexible tether that extends away from the first end of the body, wherein the removal element comprises a first configuration in which the removal element has a first size and a second configuration in which the removal element has a second size, wherein the first size is smaller than the second size, and wherein the removal element comprises a self-expanding structure that is constrained in the first configuration;
wherein the removal element is constrained in the first configuration by a constraint element comprising enteric coating material that degrades after introduction into a body such that the removal element increases from the first size to the second size over a selected period of time comprising two days or more;
and wherein the removal element is not constrained by the constraint element in the second configuration.

8. A stent according to claim 7, wherein the removal element is attached to the stent by a flexible tether.

9. A stent according to claim 7, wherein the removal element comprises a parachute-like shape in the second configuration.

10. A stent according to claim 7, wherein the removal element is attached to the stent by a flexible tether, and wherein the removal element comprises a parachute-like shape in the second configuration.

11. An implantable stent comprising:
a body comprising a first end and a second end, wherein a lumen extends through the body from the first end to the second end; and
a removal element fixedly attached to the body by a flexible tether that extends away from the first end of the body, wherein the removal element comprises a first configuration in which the removal element has a first size and a second configuration in which the removal element has a second size, wherein the first size is smaller than the second size, and wherein the removal element comprises a self-expanding structure that is constrained in the first configuration;
wherein the removal element is constrained in the first configuration by a constraint element comprising biodegradable material that degrades after introduction into a body such that the removal element increases from the first size to the second size over a selected period of time comprising two days or more;
and wherein the removal element is not constrained by the constraint element in the second configuration.

12. A stent according to claim 11, wherein the removal element is attached to the stent by a flexible tether.

13. A stent according to claim 11, wherein the removal element comprises a parachute-like shape in the second configuration.

14. A stent according to claim 11, wherein the removal element is attached to the stent by a flexible tether, and wherein the removal element comprises a parachute-like shape in the second configuration.

* * * * *